United States Patent [19]

Horwell et al.

[11] Patent Number: 5,610,176
[45] Date of Patent: Mar. 11, 1997

[54] TACHYKININ (NK1) RECEPTOR ANTAGONISTS

[75] Inventors: David C. Horwell, Foxton; William Howson, Sandwich; Martyn C. Pritchard, St. Ives, all of England

[73] Assignee: Warner-Lambert Company, Morris Plains, N.J.

[21] Appl. No.: 525,228

[22] Filed: Sep. 7, 1995

Related U.S. Application Data

[63] Continuation-in-part of Ser. No. 254,821, Jun. 6, 1994, abandoned.

[51] Int. Cl.$^6$ .................. C07D 419/06; C07D 201/10; A61K 31/40; A61K 31/495
[52] U.S. Cl. .................. 514/414; 514/415; 514/421; 514/406; 514/407; 514/359; 514/255; 514/80; 544/371; 544/373; 544/144; 544/131; 544/140; 544/143; 548/361.1; 548/491; 546/201; 546/199; 546/194; 546/275.7; 546/277.4; 546/274.7; 546/256; 546/22; 546/24; 424/9.1
[58] Field of Search .................. 548/491, 361.1; 544/371, 373; 546/282, 278; 424/2; 514/414, 415, 421, 406, 407

[56] References Cited

U.S. PATENT DOCUMENTS 5,346,907  9/1994  Kerwin, Jr. et al. .................. 514/312

FOREIGN PATENT DOCUMENTS

| | | |
|---|---|---|
| 0336356A2 | 10/1989 | European Pat. Off. . |
| 93/01165 | 1/1993 | WIPO . |
| 93/001160 | 1/1993 | WIPO . |
| 93/01169 | 1/1993 | WIPO . |
| 94/04494 | 3/1994 | WIPO . |

OTHER PUBLICATIONS

E. Schroder, et al., *Pharmazeutische Chemie*, 1982, pp. 76–83.
R. E. McMahon, *Medicinal Chemistry*, ed. A. Burger, Part I, pp. 51–52.
Lawrence, K.B., et al., *J. Med. Chem*, 1992, 35, 1273–1279.
Oury-Donat F., et al., *Neuropeptides*, 1993, 24:233.
MacLeod, A.M., et al., *J. Med. Chem*, 1993, 36, 2044–2045.
Schilling, W., et al., Abstract ML–11.3, "XIIth Intl. Symposium on Med Chem" *Conference Proceedings*, Sep. 13–17, 1992, Basel.
Co-Pending US Patent Application 08/097,264 filed Jul. 23,1993.
Nakanishi, S., *Physiological Reviews*, 1987, 67:4, 1117.
Nakanishi, S., *Annual Rev. Neurosci*, 1991, 14:123.
Tomczuk, B.E., et al., *Current Opinion in Therapeutic Patents*, 1991, 1:2, 197–210.
Snider, R.M., et al., *Science*, 1991, 251:435.
Garret, C., et al., *Proc Natl Acad Sci USA*, 1991, 88:10208–10212.
Fujii, T., et al., *Neuropeptides*, 1992, 22:24.

*Primary Examiner*—David B. Springer
*Attorney, Agent, or Firm*—Elizabeth M. Anderson

[57] ABSTRACT

The invention concerns tachykinin antagonists. The compounds are alcohols, amines and prodrugs of nonpeptides which have utility in treating disorders mediated by tachykinins. Such disorders are respiratory, inflammatory, gastrointestinal, ophthalmic, allergies, pain, vascular, diseases of the central nervous system, and migraine. Methods of preparing compounds and novel intermediates are also included.

The compounds are expected to be especially useful in asthma, multiple sclerosis, rheumatoid arthritis, the management of pain, migraine, and antiemetic agents.

25 Claims, No Drawings

TACHYKININ (NK1) RECEPTOR ANTAGONISTS

CROSS-REFERENCE TO RELATED APPLICATION

This is a continuation-in-part of U.S. application Ser. No. 08/254,821 filed Jun. 6, 1994, now abandoned.

BACKGROUND OF THE INVENTION

Over the last decade, major advances have been made in the understanding of the biology of the mammalian tachykinin neuropeptides. It is now well established that substance-P (1), neurokinin A (NKA) (2), and neurokinin B (NKB) (3), all of which share a common C-terminal sequence Phe-X-Gly-Leu-Met-$NH_2$, (Nakanishi S., *Physiol. Rev.*, 67: 117 (1987)), are widely distributed throughout the periphery and central nervous system (CNS) where they appear to interact with at least three receptor types referred to as $NK_1$, $NK_2$, and $NK_3$ (Guard S., et al., *Neurosci. Int.*, 18: 149 (1991)). Substance-P displays highest affinity for $NK_1$ receptors, whereas NKA and NKB bind preferentially to $NK_2$ and $NK_3$ receptors, respectively. Recently, all three receptors have been cloned and sequenced and shown to be members of the G-protein-linked "super family" of receptors (Nakanishi S., *Annu. Rev. Neurosci.*, 14: 123 (1991)).

Substance-P is the best known of the mammalian tachykinins and has been shown to display preferential affinity for the $NK_1$ tachykinin receptor (Guard S., Watson S. P., *Neurochem. Int.*, 18: 149 (1991)). Substance-P and the other tachykinins are suggested to play a major role in a variety of biological processes including pain transmission, vasodilation, bronchoconstriction, activation of the immune system, and neurogenic inflammation (Maggi C. A., et al., *Auton. Pharmacol.*, 13: 23 (1993)).

However, to date, a detailed understanding of the physiological roles of tachykinin neuropeptides has been severely hampered by a lack of selective, high affinity, metabolically stable tachykinin receptor antagonists that possess both good bioavailability and CNS penetration. Although several tachykinin receptor antagonists have been described (Tomczuk B. E., et al., *Current Opinions in Therapeutic Patents*, 1: 197 (1991)), most have been developed through the modification and/or deletion of one or more of the amino acids that comprise the endogenous mammalian tachykinins such that the resulting molecules are still peptides that possess poor pharmacokinetic properties and limited in vivo activities.

Since 1991, a number of high-affinity nonpeptide $NK_1$ tachykinin receptor antagonists have been identified primarily as a result of the screening of large comopund collections using high throughput radioligand binding assays. These include the fiollowing: the quinuclidine derivative, CP-96345 [Snider R. M., et al., (*Science*, 251: 435 (1991)); the piperidine derivative, CP-99994 (McLean S., et al., *J. Reg. Peptides*, S12- (1992); the perhydroisoindoione derivative, RP-67580 (Garret C., et al., *Natl. Acad. Sci., U.S.A.*, 88: 10208 (1991)); the steroid derivative, WIN 51708 (Lawrence K. B., et al., *J. Med. Chem.*, 35: 1273 (1992)); the piperidine derivative, SR-140333 (Oury-Donat F., et al., *Neuropeptides*, 24: 233 (1993)); and a tryptophan derivative (Macleod A. M., et al., *J. Med. Chem.*, 36: 2044 (1993)).

FK888, a di-peptide with high affinity for the $NH_1$ receptor, was rationally designed from the octapeptide [D-Pro[4], D-Trp[7,9,10], Phe[11]]SP(4-11) (Fujii T., et al., *Neuropeptides*, 22: 24 (1992)). Schilling, et al., have been described a series of piperidines as $NK_1$ receptor antagonists derived from a peptide/template approach (Schlling W., et al., XIIth International Symposium on Medicinal Chemistry, Basel, September 1992, Abstract ML-11.3).

Substance-P is widely distributed throughout the periphery and central nervous system. It is believed to mediate a variety of biological actions, via an interaction with three receptor types referred to as $NH_1$, $NK_2$, and $NK_3$, including smooth muscle contraction, pain transmission, neuronal excitation, secretion of saliva, angiogenesis, broncho-construction, activation of the immune system and neurogenic inflammation.

Accordingly, compunds capable of antagonizing the effects of substance-P at $NK_1$ receptors will be useful in treating or preventing a variety of brain disorders including pain, anxiety, panic, depression, schizophrenia, neuralgia, and addiction disorders; inflammatory diseases such as arthritis, asthama, and psoriasis; gastrointestinal disorders including colitis, Crohn's disease, irritable bowel syndrome, and satiety; allergic responses such as eczema and rhinitis; vascular disorders such as angina and migraine; neuropathological disorders including Parkinson's disease, multiple sclerosis, and Alzheimer's disease; and ophthalmic diseases including scleroderma.

The compounds of the invention, $NK_1$ receptor antagonists, are useful as anti-angiogenic agents for the treatment of conditions associated with aberrant neovascularization such as rheumatoid arthritis, atherosclerosis, and tumor cell growth. They will also be useful as agents for imaging $NK_1$ receptors in vivo in conditions such as ulcerative colitis and Crohn's disease.

They will also be useful as antiemetics versus emergens such as cisplatin.

International Publication Numbers WO 93/01169, WO 93/01165, and WO 93/001160 cover certain nonpeptide tachykinin receptor antagonists.

Copending U.S. application No. 08/344,064 filed Nov. 29, 1994, covers certain $NK_1$ receptor antagonists which are unique in the alkylation/substitution pattern along the backbone. That application for a patent is hereby incorporated by reference.

SUMMARY OF THE INVENTION

The invention covers tachykinin antagonists. The compounds are nonpeptides which have proved to be highly selective and functional tachykinin antagonists. These compounds are unique in the alkylation/substitution pattern along their backbone and in the alcohol, promoieties (prodrug), and amine groups which are expected to improve pharmacokinetic properties such as increased water solubility and absolute oral bioavailability.

Compounds of the invention are those of formula

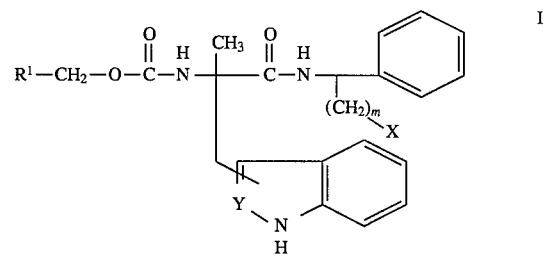

or a pharmaceutically acceptable salt thereof wherein $R^1$ is phenyl, pyridyl, thienyl, furanyl, naphthyl, indolyl, benzofuranyl, or benzothienyl each unsubstituted, mono-, di-, or trisubstituted by alkyl, hydroxy, alkoxy, nitro, halogen, amino, or trifluoromethyl;

X is $OR^2$ wherein $R^2$ is hydrogen, $(CH_2)_nNR^3R^4$ or a promoiety, or

X is $NH_2$,
NHCO-promoiety,
$NHCO(CH_2)_nNR^3R^4$,
$NR^3R^4$, or
$(CH_2)_nNR^3R^4$ wherein n is an integer of from 0 to 5 and $R^3$ and $R^4$ are each independently selected from hydrogen and methyl or $R^3$ and $R^4$ form a ring together with the N to which they are attached;

m is an integer of from 1 to 6; and

Y is CH, $CCH_3$, CF, CCl, CBr, $CSCH_3$, or N.

Preferred compounds of the instant invention are those of Formula I above wherein $R^1$ is phenyl, pyridyl, thienyl, furanyl, naphthyl, indolyl, benzofuranyl, or benzothienyl each unsubstituted or mono-, di-, or trisubstituted by alkyl, hydroxy, alkoxy, nitro, halogen, amino, or trifluoromethyl;

X is $OR^2$ wherein $R^2$ is hydrogen, $—COCH_2N(CH_3)_2$, —COMe, $—COC(CH_3)_2N(CH_3)_2$, —COCH$[CH_2CH(CH_3)_2]NH_2$, $—COCH_2CH_2CO_2H$,

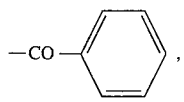

$—COC(CH_3)_3$, $—COOC(CH_3)_3$,
$—COCH(CH_2CO_2H)NH_2$, $—PO_3H_2$,

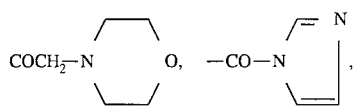

$—CO—C(CH_3)—NH—COOC(CH_3)_3$,

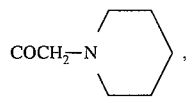

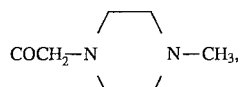

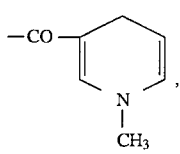

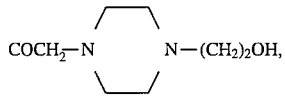

$—(CH_2)_nNR^3R^4$, or $—CHR^5NR^3R^4$ wherein $R^5$ is a side chain of a genetically coded amino acid;

X is $NHCO(CH_2)_nNR^3R^4$ or $NR^3R^4$ wherein n is an integer of from 0 to 5 and $R^3$ and $R^4$ are each independently hydrogen or methyl;

m is 1; and

Y is CH, $CCH_3$, CF, CCl, CBr, $CSCH_3$, or N.

More preferred compounds of the instant invention are those of Formula I above wherein $R^1$ is phenyl, 2-benzofuranyl, 2-fluorophenyl, 2,5-difluorophenyl, 2-benzothienyl, or 4-$CH_3$-2-fluorophenyl;

X is $OR^2$ wherein $R^2$ is hydrogen, COCH $[(CH_2CH(CH_3)_2)NH_2]$, or $COCH_2N(CH_3)_2$,

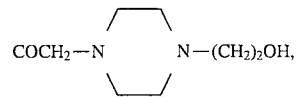

$PO_3H_2$, or

X is $NH_2$ or $NHCH_3$;

m is 1; and

Y is CH.

Most preferred compounds of the invention are:

Carbamic acid, [2-[(2-hydroxy-1-phenylethyl)amino]-1-(1H-indol-3-ylmethyl)-1-methyl-2-oxoethyl]-, 2-benzofuranylmethyl ester, [R-(R*,R*)]-;

Carbamic acid, [2-[(2-hydroxy-1-phenylethyl)amino]-1-(1H-indol-3-ylmethyl)-1-methyl -2-oxoethyl]-, (2-fluorophenyl)methyl ester, [R-(R*,R*)]-;

Carbamic acid, [2-[(2-hydroxy-1-phenylethyl)amino]-1-(1H-indol-3-ylmethyl)-1-methyl-2-oxoethyl]-, (2,5-difluorophenyl)methyl ester, [R-(R*,R*)]-(+)-isomer;

Carbamic acid, [2-[(2-hydroxy-1-phenylethyl)amino]-1-(1H-indol-3-ylmethyl)-1-methyl-2-oxoethyl]-, benzo[b]thien-2-ylmethyl ester, [R-(R*,R*)]-;

Glycine, N,N-dimethyl-, 2-[[2-[[(2-benzofuranylmethoxy)carbonyl]amino]-3-(1H-indol-3-yl)-2-methyl-1-oxopropyl]amino]-2-phenylethyl ester, monohydrochloride, [R-(R*,R*)]-;

L-Leucine, 2-[[2-[[(2-benzofuranylmethoxy)carbonyl]amino]-3-(1H-indol-3-yl)-2-methyl-1-oxopropyl]amino]-2-phenylethyl ester, [R-(R*,R*)]-;

Carbamic acid, [2-[(2-amino-1-phenylethyl)amino]-1-(1H-indol-3-ylmethyl)-1-methyl-2-oxoethyl]-, 2-benzofuranylmethyl ester, [R-(R*,R*)]-;

Carbamic acid, [2-[(2-amino-1-phenylethyl)amino]-1-(1H-indol-3-ylmethyl)-1-methyl-2-oxoethyl]-, 2-benzofuranylmethyl ester, [R-(R*,R*)]-;

Carbamic acid, [1-(1H-indol-3-ylmethyl)-1-methyl-2-oxo-2-[(1-phenylethyl)amino]ethyl]-, phenylmethyl ester, [R-(R*,R*)]-;

Carbamic acid, [2-(2-hydroxy-1-phenylethyl)amino]-1-(1H-indol-3-ylmethyl)-1-methyl-2-oxoethyl]-, 2-benzofuranylmethyl ester, [R-(R*,R*)]-;

Carbamic acid, [2-[[(2-[[(dimethylamino)acetyl]-amino]-1-phenylethyl]amino]-1-(1H-indol-3-ylmethyl)-1-methyl-2-oxoethyl]-, 2-benzofuranylmethyl ester, monohydrochloride, [R-(R*,R*)]-; and

[2-(1H-Indol-3-yl)-1-methyl-1-(1-phenyl)-2-phosphonooxy-ethylcarbamoyl)-ethyl]-carbamic acid benzofuran-2-ylmethyl ester monosodium salt.

Novel intermediates of the final products are also included. They are compounds of Formula II

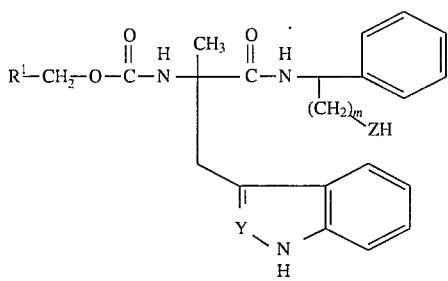

wherein $R^1$ is phenyl, pyridyl, thiophenyl, furanyl, naphthyl, indolyl, benzofuranyl, or benzothienyl each unsubstituted or mono-, di-, or trisubstituted by alkyl, hydroxy, alkoxy, nitro, halogen, amino, or trifluoromethyl;

m is an integer of from 1 to 6; and,

Y is CH, $CCH_3$, CF, CCl, CBr, $CSCH_3$, or N; and

Z is oxygen or NH.

Another aspect of the invention is a pharmaceutical composition comprising an amount of a compound according to Formula I effective to treat respiratory disorders in a mammal suffering therefrom, and a pharmaceutically acceptable carrier.

Another aspect of the invention is a method for treating respiratory disorders in a mammal such as a human comprising administering a therapeutically effective amount of a compound according to Formula I.

Another aspect of the invention is a pharmaceutical composition comprising an amount of a compound according to Formula I effective to treat inflammation in a mammal suffering therefrom, and a pharmaceutically acceptable carrier.

Another aspect of the invention is a method for treating inflammation in a mammal such as a human comprising administering a therapeutically effective amount of a compound according to Formula I.

Another aspect of the invention is a pharmaceutical composition comprising an amount of a compound according to Formula I effective to treat gastrointestinal disorders in a mammal suffering therefrom, and a pharmaceutically acceptable carrier.

Another aspect of the invention is a method for treating gastrointestinal disorders in a mammal such as a human comprising administering a therapeutically effective amount of a compound according to Formula I.

Another aspect of the invention is a pharmaceutical composition comprising an amount of a compound according to Formula I effective to treat eye diseases such as dry eye and conjunctivitis in a mammal suffering therefrom, and a pharmaceutically acceptable carrier.

Another aspect of the invention is a method for treating eye diseases in a mammal such as a human comprising administering a therapeutically effective amount of a compound according to Formula I.

Another aspect of the invention is a pharmaceutical composition comprising an amount of a compound according to Formula I effective to treat allergies in a mammal suffering therefrom, and a pharmaceutically acceptable carrier.

Another aspect of the invention is a method for treating allergies in a mammal such as a human comprising administering a therapeutically effective amount of a compound according to Formula I.

Another aspect of the invention is a pharmaceutical composition comprising an amount of a compound according to Formula I effective to treat diseases of the central nervous system in a mammal suffering therefrom, and a pharmaceutically acceptable carrier.

Another aspect of the invention is a method for treating diseases of the central nervous system in a mammal such as a human comprising administering a therapeutically effective amount of a compound according to Formula I.

Another aspect of the invention is a pharmaceutical composition comprising an amount of a compound according to Formula I effective to treat migraine in a mammal suffering therefrom, and a pharmaceutically acceptable carrier.

Another aspect of the invention is a method for treating migraine in a mammal such as a human comprising administering a therapeutically effective amount of a compound according to Formula I.

Another aspect of the invention is a pharmaceutical composition comprising an amount of compound according to Formula I effective to treat pain arising from neurogenic inflammation or inflammatory pain.

Another aspect of the invention is a method for treating pain such as pain arising from neurogenic inflammation in inflammatory pain status.

Another aspect of the invention is a pharmaceutical composition comprising an amount of a compound according to Formula I effective in treating conditions associated with aberrant neovascularization: rheumatoid arthritis, multiple sclerosis, atherosclerosis, and tumor cell growth.

Another aspect of the invention is a method of treating conditions associated with aberrant neovascularization: rheumatoid arthritis, multiple sclerosis, atherosclerosis, and tumor cell growth.

Another aspect of the invention is a pharmaceutical composition comprising an amount of a compound according to Formula I effective in treating emesis associated with such emergins as cisplatin.

Another aspect of the invention is a method of treating conditions associated with emesis.

Another aspect of the invention is using the compounds as imaging agents for imaging $NK_1$ receptors in vivo.

Processes for preparing the compounds and novel intermediates are included in the invention.

DETAILED DESCRIPTION OF THE INVENTION

The following terms are descriptive of the compounds of the instant invention.

The alkyl groups contemplated by the invention include straight or branched carbon chains of from 1 to 8 carbon atoms except where specifically stated otherwise. Representative groups are methyl, ethyl, propyl, isopropyl, n-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl, and the like.

The alkoxy groups contemplated by the invention comprise both straight and branched carbon chains of from 1 to 6 carbon atoms unless otherwise stated. Representative groups are methoxy, ethoxy, propoxy, i-propoxy, t-butoxy, and hexoxy.

The term halogen is intended to include fluorine, chlorine, bromine, and iodine.

$R^1$ is an aryl or a heterocycle which is unsubstituted or bears from 1 to 3 substituents. Aryl groups include phenyl, naphthyl, biphenyl, and indanyl. Preferred aryl groups are phenyl and naphthyl.

Heterocyclic groups include pyridyl, 2- or 3-indolyl, benzofuranyl, furanyl, benzothienyl, thienyl. Preferred heterocyclic groups are: benzofuranyl and benzothienyl.

The substituents in the above are selected from alkyl, hydroxy, alkoxy, nitro, halogen, amino, and trifluoromethyl. From 1 to 3 substituents are considered. Preferred substituents are fluorine, methoxy, methyl, and amino; most preferred is 1,2-dimethoxy.

The promoiety of the instant invention are found in the X term of Formula I above. These moieties are useful in that they provide improved drug stability, improved water solubility, enhanced absorption, allow for site-specific delivery, mask side effects, and/or extend the duration of action (Bundgaard H., Elsevier E., *Design of Prodrugs*, 1985). In the instant invention, various promoieties such as the following are useful: $-COCH_2N(CH_3)_2$, $-COC(CH_3)_2N(CH_3)_2$, $-COCH[(CH_2CH(CH_3)_2)]NH_2$, $-COCH(CH_2CO_2H)NH_2$, $-PO_3H_2$,

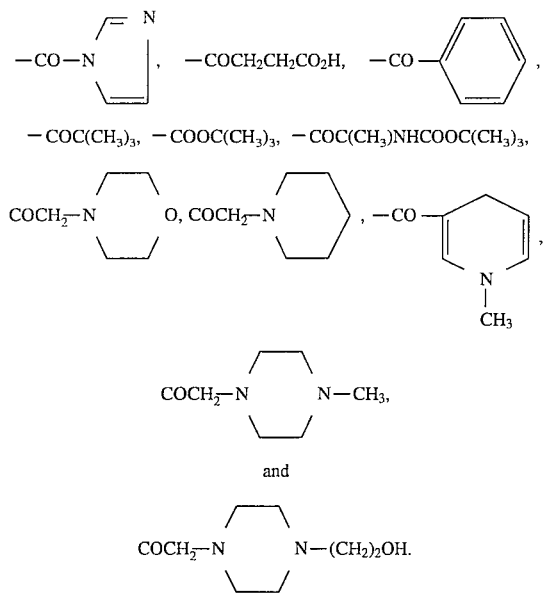

Others as would occur to a skilled artisan are also included.

As shown in Table I below, the compounds of the invention are tachykinin $NK_1$ receptor antagonists in an in vitro $NK_1$ preparation, i.e., the compound antagonizes the pharmacological action of the selective $NK_1$ receptor agonist substance-P methylester on this tissue. Therefore, it is expected to be useful in the therapeutic disorders when the attenuation of the $NK_1$ receptor response is the appropriate form of intervention.

TABLE I

| | $NK_1$ Antagonist Activity |
|---|---|
| Example | $K_B$ (nM) Guinea Pig Ileum* |
| 6 | 1.3 |
| 16 | 10.6 |
| 17 | 9.3 |
| 18 | 6.3 |
| 9 | 6.2 |
| 12 | 22 |
| 8 | 16 |

*McKnight A.T., et al., Br. J. Pharmacol., 104:355–360 (1991)

These compounds are active in vivo as $NK_1$ receptor antagonists as shown in Table II below. They antagonize the ability of a $NK_1$ receptor selective agonist (SPOMe) to induce plasma protein extravasation in the guinea pig bladder. The protocol is similar to that described by Eglezos, et al., *Eur. J. Pharmacol.*, 209: 277–279 (1991).

TABLE II

| Guinea Pig Plasma Extravasation (Bladder) | | |
|---|---|---|
| Example | $ID_{50}$ (mg/kg IV) | $ID_{50}$ (mg/kg PO) |
| 6 | 0.16 | 30 |
| 9 | 0.16 | 4.4 |

As can be seen from the binding data below (Table III), several of these compounds have high affinity for the $NK_1$ receptor.

TABLE III

| $NK_1$ Binding in Human IM9 Lymphoma Cells | |
|---|---|
| Example | $IC_{50}$ (nM) |
| 6 | 1.2 |
| 9 | 12 |
| 12 | 16 |
| 10 | 84 |
| 8 | 13 |
| 15 | 58 |
| 16 | 3.3 |
| 17 | 3.9 |
| 18 | 9 |

Table III above shows the concentration of the compounds of the present invention which is needed to displace 50% of a specific radioligand ($[^{125}I]$Bolton Hunter Substance-P) from tachykinin $NK_1$ receptor sites in human IM9 lymphoma cells (Boyle S., et al., Rational design of high affinity tachykinin $NK_1$ receptor antagonists. *Bioorg. Med. Chem.*, 1994, in press).

Compounds of the invention are expected to be useful in treating disorders mediated by tachykinins such as respiratory disorders, especially asthma.

They are also expected to be useful in treating inflammation such as arthritis, gastrointestinal disorders such as colitis, Crohn's disease, and irritable bowel syndrome.

They are further expected to be useful in treating and/or preventing eye diseases such as dry eye and conjunctivitis.

They are further expected to be useful in treating allergies such as rhinitis (common cold), and eczema.

The compounds are expected to treat vascular disorders such as angina and migraine.

They are further expected to be useful in preventing and/or treating diseases of the central nervous system such as schizophrenia.

They are further expected to be useful in the management of pain.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The compounds of the invention include solvates, hydrates, pharmaceutically acceptable salts, and polymorphs (different crystalline lattice descriptors) of the compounds of Formula I.

The compounds of the present invention can have multiple chiral centers in the above Formula I depending on their structures. In particular the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by conventional methods well known in the art such as conversion to a salt with an optically active compound, followed by separation by chromatography or recrystallization and reconversion to the nonsalt form.

Where it is appropriate to form a salt, the pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, gluceptate, gluconate, glutamate, glycoloylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, theoclate, triethiodide, benzathine, chloroprocaine, choline, diethanolamine, ethylenediamine, meglumine, procaine, aluminum, calcium, lithium, magnesium, potassium, sodium, and zinc.

Cyclodextrin is one suitable inclusion in a pharmaceutical preparation.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of the instant invention are prepared as summarized below in Scheme I and as described below in Examples 1–18.

SCHEME I
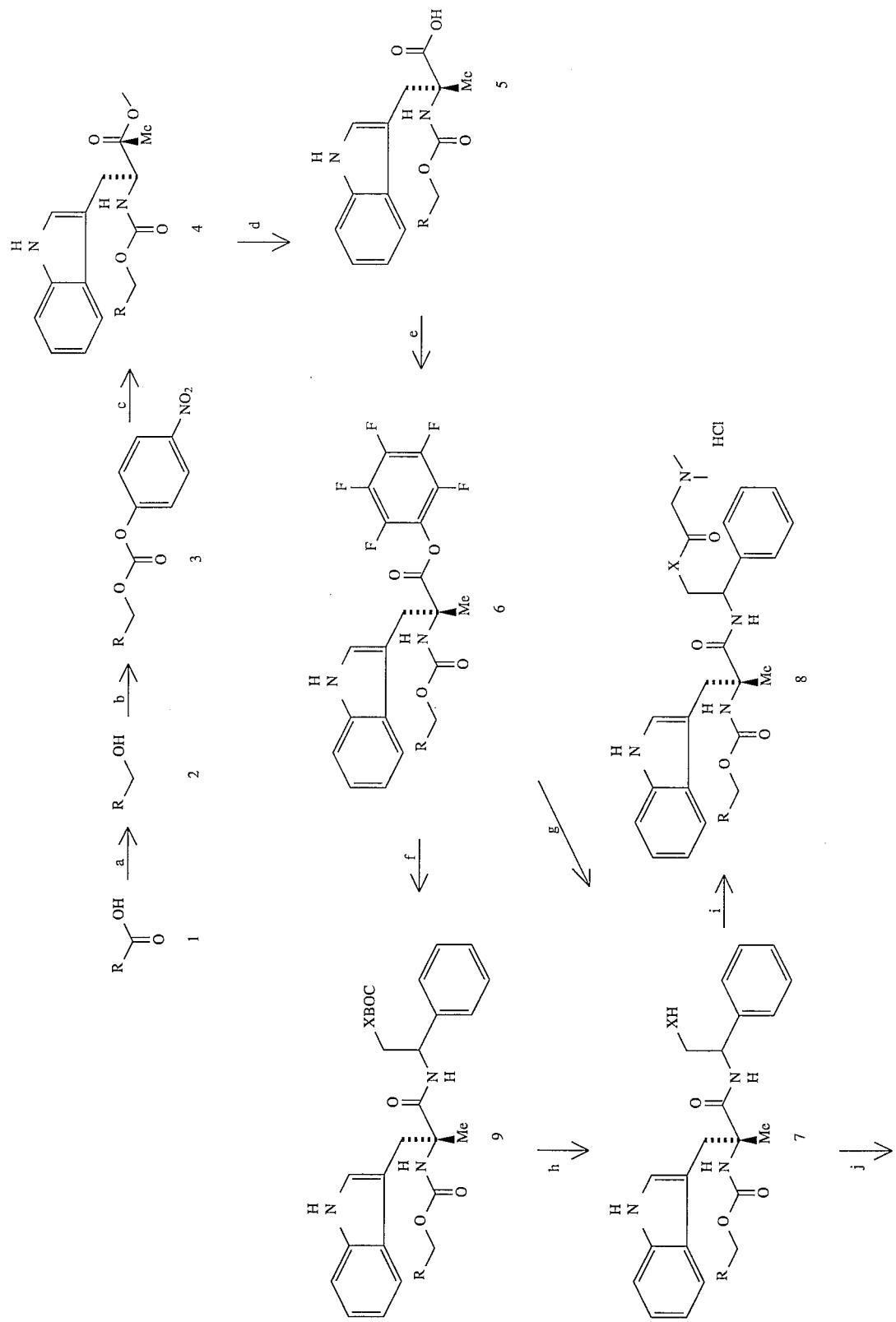

-continued
SCHEME 1

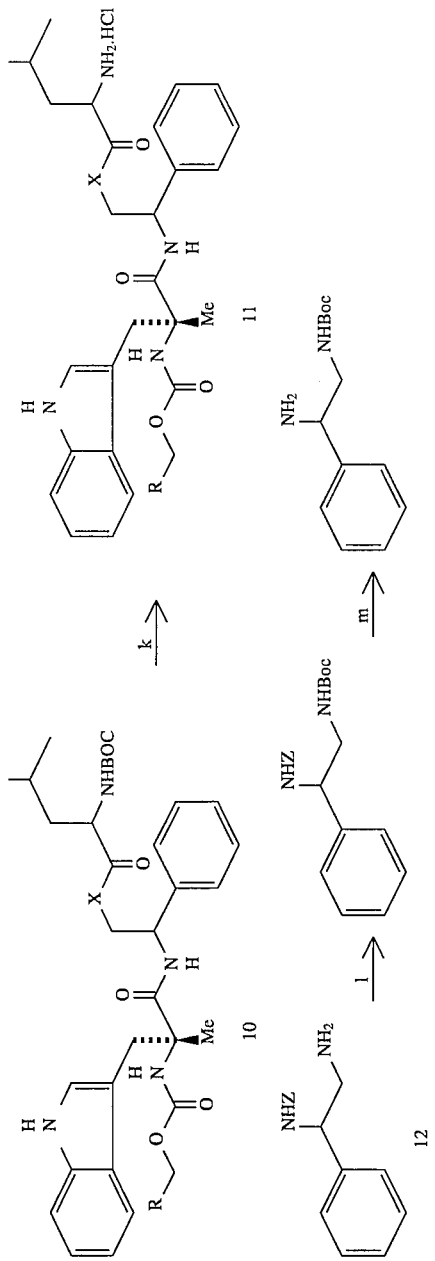

Compounds 1 to 7: (i) X = O, R = Ph; (ii) X = O, R = 2-F, Ph; (iii) X = O, R = 2,5-DiF, Ph; (iv) X = O, R = 2-benzofuran; (v) X = O, R = 2-benzothiophene; (vi) X = NH, R = 2-benzofuran.

Compounds 8 and 9: (i) X = O, R = 2-benzofuran; (ii) X = NH, R = 2-benzofuran.

Compounds 10 and 11: (i) X = O, R = 2-benzofuran.

Reagents and conditions: (a) LiAlH$_4$, THF, −5° C. to 25° C.; (b) Pyridine, CH$_2$Cl$_2$, p-NO$_2$PhOCOCl; (c) (R) αMeTrp(OMe), DMAP, DMF; (d) LiOH, THF, MeOH, H$_2$O; (e) DCCI, PFP, EtOAc; (f) (R) β NH$_2$, N-BocPhenethylamine 14, EtOAc; (g) (R)Phenylglycinol, EtOAc; (h) Formic acid; (i) N,N-DiMe$_2$Gly, DCCI, DMAP, CH$_2$CH$_2$; (j) Boc- (L) -Leu(OH).

SCHEME II
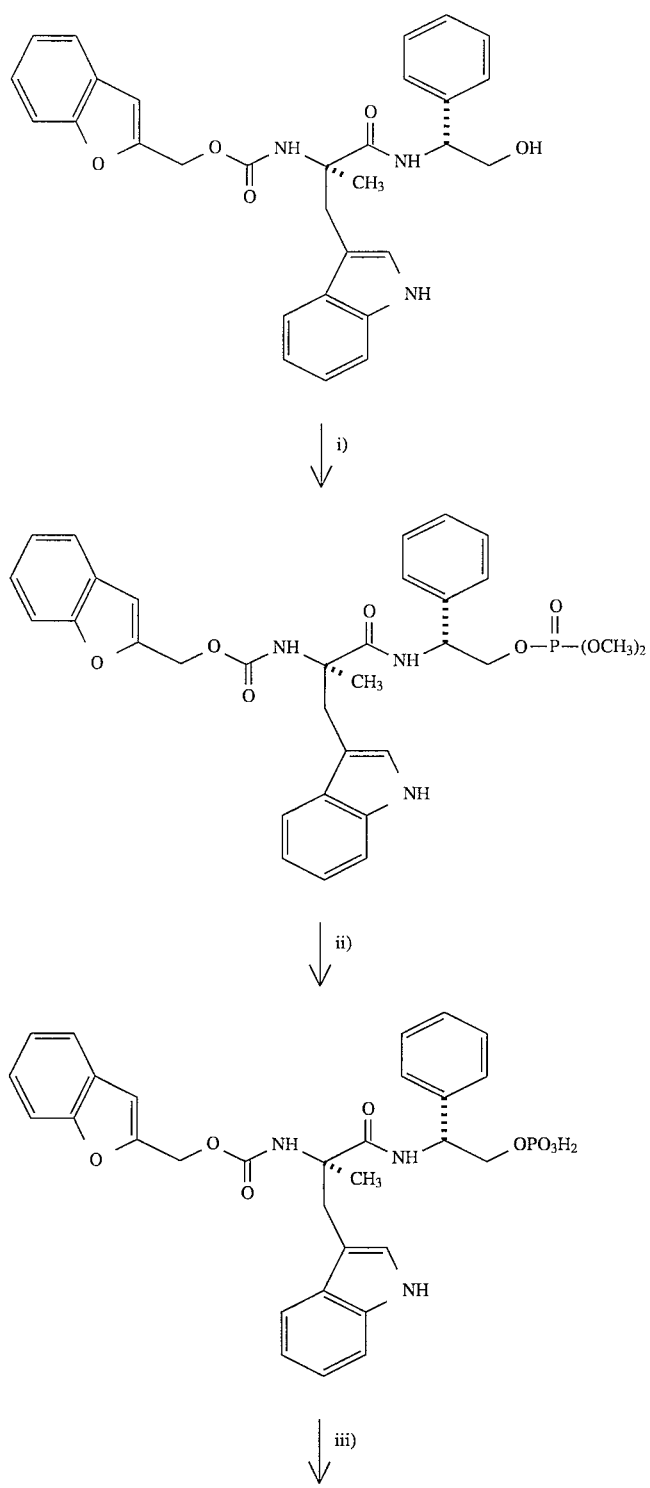

-continued
SCHEME II

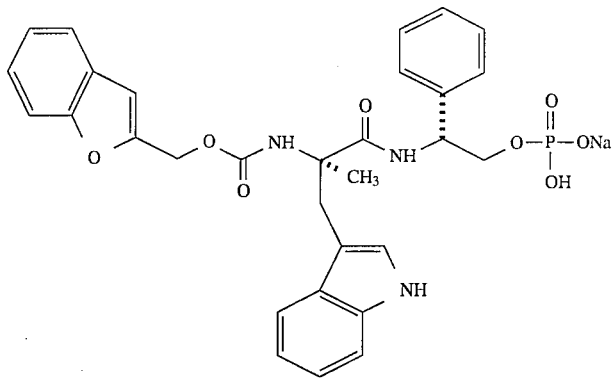

Reagents and conditions:
i) Di-t-butyl-N, N-diethylphosphoramidite, 1-H-tetrazole, MCPBA, THF, 0° C.
ii) Formic acid, room temperature
iii) NaOH, H₂O/Acetone, room temperature The following examples are not intended to be limiting of the invention, rather, they are illustrative.

EXAMPLE 1

Compound 2 (iv)

To a suspension of lithium aluminum hydride (2.82 g, 63 mmol) in dry THF (150 mL) at −5° C. under nitrogen was added dropwise a solution of benzofuran-2-carboxylic acid (10.2 g, 63 mmol) in THF (100 mL). The reaction mixture was allowed to warm to room temperature and stirred for 16 hours. 1N HCl was added slowly with cooling (cardice-acetone bath) and the resulting solution was washed with 1N HCl, NaHCO$_{3(aq)}$, dried (MgSO$_4$) and the solvent removed in vacuo. The residue was purified by flash chromatography on silica eluting with a mixture of hexane:EtOAc (1:1) to give 2 (iv) as a yellow oil (7.2 g, 77%).

$^1$H NMR (CDCl$_3$): δ 2.68 (1H, s, O$\underline{H}$), 4.70 (2H, s, C$\underline{HH}$OH), 6.58 (1H, s, Ar$\underline{H}$3), 7.15–7.27 (2H, m, Ar$\underline{H}$), 7.42 (1H, d, 8.1 Hz, Ar$\underline{H}$), 7.48–7.51 (1H, m, Ar$\underline{H}$);

Anal. C$_9$H$_8$O$_2$: C, H, N.

EXAMPLE 2

Compound 3 (iv)

To a stirred solution of 2 (iv) (8.58 g, 58 mmol) and pyridine (4.82 mL, 58 mmol) in CH$_2$Cl$_2$ (150 mL) at 10° C. was added dropwise a solution of p-nitrophenyl chloroformate (14 g, 70 mmol) in CH$_2$Cl$_2$ (150 mL). The reaction mixture was allowed to warm to room temperature and stirred for 18 hours. The solvent was removed in vacuo and the residue taken up in EtOAc, washed with 1N HCl, NaHCO$_{3(aq)}$, dried (MgSO$_4$), and concentrated in vacuo. The resultant yellow solid was purified using hexane:ether (9:1) as eluant to give 3 (iv) as a cream solid (9.8 g, 54%).

$^1$H NMR (CDCl$_3$): δ 5.41 (2H, s, C$\underline{HH}$O), 6.90 (1H, s, $\underline{H}$2 of benzofuran), 7.21–7.42 (2H, m, Ar$\underline{H}$), 7.39 (2H, d, 9.2 Hz, $\underline{H}$2, $\underline{H}$6 of phenyl), 7.52 (1H, d, 7.8 Hz, Ar$\underline{H}$), 7.60 (1H, d, 7.1 Hz, Ar$\underline{H}$), 8.28 (2H, d, 9.2 Hz, $\underline{H}$3, $\underline{H}$5 of phenyl);

IR: 3119.0, 1770.0, 1617.0, 1594.0, 1524.0, 1346.0, 1251.0, 1213.0, 862.0, 753.0 cm$^{-1}$; mp 90.5°–92.5° C.;

Anal. C$_{16}$H$_{11}$NO$_6$: C, H, N.

EXAMPLE 3

Compound 4 (iv)

The mixed carbonate 3 (iv) (7 g, 22 mmol), (R)α-methyltryptophan, methyl ester (5.2 g, 22 mmol), and dimethylaminopyridine (2.7 g, 22 mmol) were stirred in DMF (60 mL) at room temperature overnight. The reaction mixture was taken up in ether, washed with NaCO$_{3(aq)}$, 1N HCl, dried (MgSO$_4$), and concentrated in vacuo. The residue was purified by flash chromatography on silica gel eluting with hexane:EtOAc (7:3) to give 4 (iv) as a yellow sticky solid (8.57 g, 96%).

$^1$H NMR (CDCl$_3$): δ 1.70 (3H, s, αCH$_3$), 3.36 (1H, d, 14.6 Hz, C$\underline{HH}$ indole), 3.54 (1H, bd, 13.9 Hz, CH$\underline{H}$ indole), 3.67 (3H, s, CO$_2$C$\underline{H}_3$), 5.17 (1H, d, 13.4 Hz, C$\underline{HH}$OCONH), 5.27 (1H, d, 13.2 Hz, CH$\underline{H}$OCONH), 5.58 (1H, bs, OCON$\underline{H}$), 6.78 (1H, s, Ar$\underline{H}$), 6.81 (1H, s, Ar$\underline{H}$), 7.00 (1H, t, 7.6 Hz, Ar$\underline{H}$), 7.12 (1H, t, 7.3 Hz, Ar$\underline{H}$), 7.23–7.34 (3H, m, Ar$\underline{H}$), 7.47–7.50 (2H, m, Ar$\underline{H}$), 7.81 (1H, bs, indole N$\underline{H}$).

EXAMPLE 4

Compound 5 (iv)

To a solution of 4 (iv) (8.57 g, 21 mmol) in THF (90 mL) was added lithium hydroxide (30 mL, 10M), methanol (30 mL) and water (60 mL) and the reaction was stirred at room temperature for 2 days. The volatiles were removed in vacuo and the aqueous mixture was acidified with 1N HCl, and extracted with EtOAc. The organic phase was washed with water, dried (MgSO$_4$), and concentrated in vacuo to yield 5 (iv) as a yellow oil (8.23 g, 100%) which was used without further purification in the next step.

EXAMPLE 5

Compound 6 (iv)

To a solution of 5 (iv) (8.23 g, 21 mmol) in EtOAc was added dicyclohexylcarbodiimide (4.3 g, 21 mmol) followed by pentafluorophenol (3.86 g, 21 mmol) and the mixture was stirred at room temperature for 16 hours. The mixture was cooled to 0° C. for 30 minutes and the resulting precipitate of dicyclohexylurea was removed by filtration. The filtrate was washed with 1N HCl, NaCO$_{3(aq)}$, dried (MgSO$_4$), and the solvents removed in vacuo. The residue was purified by flash chromatography on silica gel eluting with a mixture of hexane: EtOAc (9:1 ) to give 6 (iv) as a cream solid (7.5 g, 64%).

$^1$H NMR (CDCl$_3$): δ 1.74 (3H, s, αCH$_3$), 3.44 (1H, d, 14.9 Hz, CHH indole), 3.66 (1H, d, 14.6 Hz, CHH indole), 5.18–5.29 (3H, m, CHHOCONH), 6.79 (1H, s, ArH), 7.0 (1H, s, ArH), 7.04 (1H, t, 7.6 Hz, ArH), 7.18 (1H, t, 7.5 Hz, ArH), 7.21–7.36 (3H, m, ArH), 7.46 (1H, d, 8.1 Hz, ArH), 7.55–7.58 (2H, m, ArH), 8.02 (1H, bs, indole NH);

IR: 3418.0, 1785.0, 1707.0, 1652.0, 1520.0, 1455.0, 1254.0 cm$^{-1}$;

MS m/e (CI) 559 (M+H);

Anal. C$_{28}$H$_{19}$F$_5$N$_2$O$_5$: C, H, N.

EXAMPLE 6

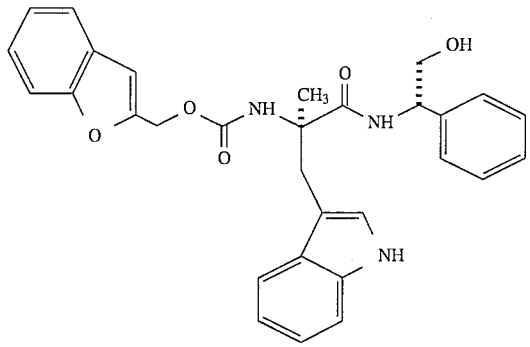

Carbamic acid,
[2-[(2-hydroxy-1-phenylethyl)amino]-1-(1H-indol-3-ylmethyl)-1-methyl-2-oxoethyl]-,
2-benzofuranylmethyl ester, [R-(R*,R*)]-

Compound 7 (IV)

The pentafluoroester 6 (iv) (5 g, 9.0 mmol) and (R)-phenylglycinol (1.27 g, 9.0 mmol) were stirred at room temperature in EtOAc (400 mL) for 24 hours. The reaction mixture was washed with 1N HCl, NaCO$_{3(aq)}$, dried (MgSO$_4$), and concentrated in vacuo. The residue was purified on silica gel by flash chromatography, eluting with a gradient of hexane:EtOAc (1:1) to EtOAc. The alcohol 7 (iv) was obtained as a white solid (3.61 g, 79%).

$^1$H NMR (CDCl$_3$): δ 1.68 (3H, s, αCH$_3$), 2.58 (1H, bs, OH), 3.23 (1H, d, 14.8 Hz, CHH indole), 3.42 (1H, d, 14.8 Hz, CHH indole), 3.63–3.72 (1H, m, CHHOH), 3.73–3.81 (1H, m, CHHOH), 5.00 (1H, m, CHCH$_2$OH), 5.13 (1H, d, 13.2 Hz, CHHOCONH), 5.25 (1H, d, 13.2 Hz, CHHOCONH), 5.45 (1H, s, NHCO), 6.52 (1H, d, 7.7 Hz, NHCHCHHOH), 6.77 (1H, s, ArH), 6.90 (1H, d, 2.0 Hz, ArH), 7.07–7.34 (10H, m, ArH), 7.46 (1H, d, 7.6 Hz, ArH), 7.57 (2H, t, 8.8 Hz, ArH), 7.59 (1H, s, indole NH);

IR: 3383.0, 1713.0, 1652.0, 1495.0, 1455.0, 1250.0, 1070.0 cm$^{-1}$;

MS m/e (FAB) 512.0 (M+H), 534.0 (M+Na); [α$_D$]=34.67 (MEOH, c=0.075); mp 77°–85° C.;

HPLC R.T.=11.943, C$^{18}$ reverse phase, 40–100% MeCN:TFA/water:TFA.

Anal. C$_{30}$H$_{29}$N$_3$O$_5$·0.35H$_2$O: C,H,N.

EXAMPLE 7

Compound 9 (ii)

The pentafluorophenyl ester 6 (iv) (1.0 g, 1.80 mmol), and α-amino, N-Boc-phenethylamine (14) (0.57 g, 2.00 mmol) were stirred at room temperature in EtOAc (100 mL) for 2 days. The reaction mixture was washed with 1N HCl, NaHCO$_{3(aq)}$, dried (MgSO$_4$), and concentrated in vacuo. The residue was purified on silica gel by flash chromatography, eluting with a gradient of hexane: EtOAc (1:1) to EtOAc. The N-protected amine was obtained as a white solid (0.87 g, 80%).

$^1$H NMR (CDCl$_3$): δ 1.41 (9H, s, tbutyl), 1.67 (3H, s, αCH$_3$), 3.25–3.31 (1H, m, CHHNHBoc), 3.42–3.39 (3H, m, CHHNHBoc, CHH indole), 4.91–5.00 (2H, m, CHCH$_2$NHBoc), 5.16 (1H, d, 13.2 Hz, CHHOCONH), 5.23 (1H, d, 13.4 Hz, CHHOCONH), 5.56 (1H, s, NHCO$_2$CH$_2$), 6.76 (1H, s, ArH), 6.81 (1H, s, ArH), 7.04 (1H, t, 7.3 Hz, ArH), 7.12–7.32 (9H, m, 8 ArH, CONHCHHPh), 7.44–7.60 (4H, m, ArH), 7.82 (1H, s, indole NH);

IR: 3354.0, 1700.3, 1652.0, 1495.0, 1455.0, 1367.0, 1251.0, 1167.0, 1069.0 cm$^{-1}$;

MS m/e (FAB) 610 (M), 611.3 (M+H), 633.1 (M+Na);

α$^D$=+7.62 (MEOH, c=0.105 g, 100 mL$^{-1}$); mp 79°–83° C.;

HPLC R.T.=15.767, C$^{18}$ reverse phase, 40–100% MeCN:TFA/water:TFA;

Anal. C$_{35}$H$_{38}$N$_4$O$_6$: C, H, N.

EXAMPLE 8

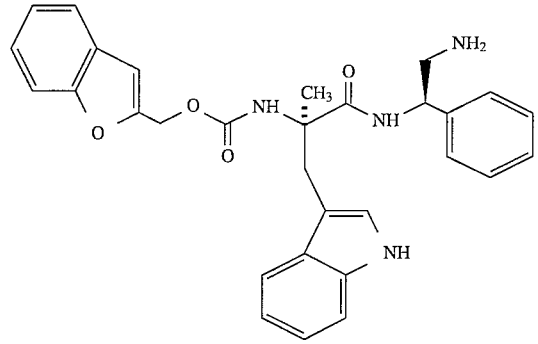

Carbamic acid,
[2-[(2-amino-1-phenylethyl)amino]-1-(1H-indol-3-ylmethyl)-1-methyl-2-oxoethyl]-,
2-benzofuranylmethyl ester [R-(R*,R*)]-

Compound 7 (VI)

A solution of formic acid (20 mL) and 9 (ii) (0.87 g, 1.43 mmol) was stirred for 1 hour. The solvent was removed and the residue was taken up in EtOAc and washed with NaHCO$_{3(aq)}$, brine, dried (MgSO$_4$), and concentrated in vacuo. The residue was triturated with EtOAc to yield the free amine as a white solid (38 rag, 52%).

$^1$H NMR (CDCl$_3$): δ 1.69 (3H, s, αCH$_3$), 2.74 (1H, dd, 4.6, 12.7 Hz, CHHNH$_2$), 2.84 (1H, dd, 5.86, 12.94 Hz, CHHNH$_2$), 3.29 (1H, d, 14.7 Hz, CHH indole), 3.44 (1H, d, 14.9 Hz, CHH indole), 4.88 (1H, m, CHCH$_2$NH$_2$), 5.15 (1H, d, 13.2 Hz, CHHOCONH), 5.23 (1H, d, 13.4 Hz, CHHOCONH), 5.58 (1H, s, NHCO$_2$CH$_2$), 6.76 (1H, s, ArH), 6.83 (1H, s, ArH), 6.88 (1H, d, 7.6 Hz, CONHCH), 7.05–7.32 (12H, m, 10 ArH, NH$_2$), 7.46 (1H, d, 8.1 Hz, ArH), 7.56 (2H, t, 8.3 Hz, ArH), 8.00 (1H, s, indole NH);

IR: 3299.0, 1719.0, 1655.0, 1493.0, 1454.0, 1250.0 cm$^{-1}$;

MS m/e (FAB) 511.5 (M+H);

α$^D$=0.00 (MEOH, c=0.105 g, 100 mL$^{-1}$); mp 166°–167° C.;

Anal. C$_{30}$H$_{30}$N$_4$O$_4$: C, H, N.

EXAMPLE 9

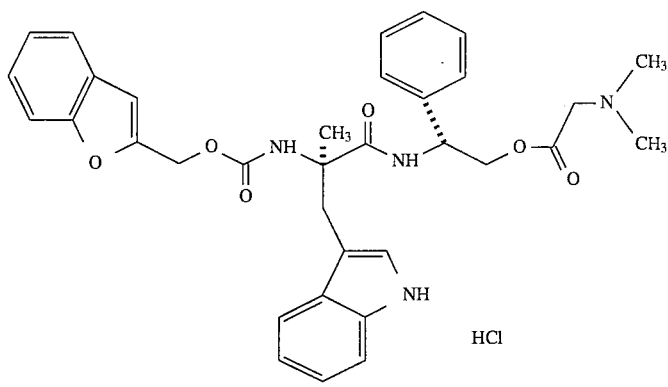

Glycine, N,N-dimethyl-, 2-[[2-[[(2-benzofuranyl-methoxy)carbonyl]amino]-3-(1H-indol-3-yl)-2-methyl-1-oxopropyl]amino]-2-phenylethyl ester, monohydrochloride, [R-(R*,R*)]-;

Compound 8 (i)

To a stirred solution of 7 (iv) (0.3 g, 0.59 mmol) in $CH_2Cl_2$ (100 mL) was added N,N-dimethylglycine (0.24 g, 2.3 mmol), dicyclohexylcarbodiimide (0.19 g, 1.8 mmol) and dimethylaminopyridine (72 mg, 0.59 mmol) and the reaction mixture was stirred at room temperature for 24 hours. The solvent was removed in vacuo and the residue, taken up in EtOAc and chilled at 4° C. for 30 minutes. The resulting white precipitate of dicyclohexylurea was removed by filtration and the filtrate was washed, dried ($MgSO_4$), and concentrated in vacuo. The residue was purified by flash chromatography on silica gel using a hexane:EtOAc (1:1) to EtOAc gradient as eluant. The sticky solid obtained was triturated with ether to produce the free dimethylamine as a white solid. To a solution of the free amine in EtOAc was added one equivalent of HCl in dioxan (0.3 mL, 4M) causing the hydrochloride salt to precipitate out. The salt was filtered and washed thoroughly with ether before repeated triturations with EtOAc/ether mixtures yielded 8 (i) as a crystalline white solid (0.17 g, 48%).

$^1$H NMR (DMSO): δ 1.27 (3H, s, αCH$_3$), 3.14 (1H, d, 14.8 Hz, CHH indole), 2.77 (6H, s, N(CH$_3$)$_2$), 3.40 (1H, d, 14.8 Hz, CHH indole), 3.95–4.10 (2H, m, OCOC HHN(CH$_3$)$_2$), 4.30–4.44 (2H, m, CHCHHOCO), 5.14–5.25 (3H, m CHCH$_2$OCO, CHHOCONH), 6.80 (1H, t, 7.2 Hz, Ar H), 6.89–6.97 (3H, m, ArH), 7.13 (1H, s, ArH), 7.22–7.41 (8H, m, ArH), 7.52 (1H, d, 8.0 Hz, ArH or NHCH), 7.61 (1H, d, 8.0 Hz, NHCH or ArH), 8.31 (1H, d, 8.4 Hz, N HCH or ArH), 10.18 (1H, bs OCONH), 10.84 (1H, s, indole NH);

IR: 3346.0, 2363.0, 1721.0, 1654.0, 1455.0, 1250.0 cm$^{-1}$;

MS m/e (CI) 597.2 (M–Cl);

$α^D$=+14.74 (MEOH, c=0. 286); mp 107°–111° C.;

HPLC R.T.=16.613, C$^{18}$ reverse phase, 20–80% MeCN:TFA/water:TFA; Anal. $C_{34}H_{37}N_4O_6Cl·1.0H_2O$: C, H, N.

EXAMPLE 10

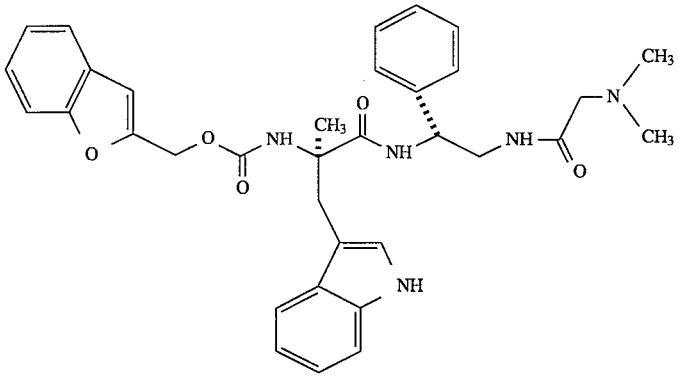

Carbamic acid, [2-[[(2-[[(dimethylamino)acetyl] amino]-1-phenylethyl]amino]-1-(1H-indol-3-ylmethyl)-1-methyl-2-oxoethyl]-, 2-benzofuranylmethyl ester, monohydrochloride, [R-(R*,R*)]-

Compound 8 (ii)

To a stirred solution of N,N-dimethylglycine (51.5 mg, 0.5 mmol) and 2-(1H-benzotriazol-1-yl)-1,1,3,3-tetramethyluronium hexafluorophosphate (HBTU) (51.5 mg, 0.50 mmol) in DMF (50 mL) at room temperature was added diisopropylethylamine (180 mL, 1.00 mmol). After 10 minutes, 7 (vi) (255 mg, 0.50 mmol) and diisopropylethylamine (90 mL, 0.50 mmol) were added to the reaction mixture which was stirred for a further 10 hours. The solvent was removed under reduced pressure and the residue was taken up in EtOAc and washed with NaHCO$_{3(aq)}$, water, brine, dried (MgSO$_4$), and concentrated in vacuo. The residue was purified by flash chromatography on silica gel using a EtOAc to 10% MeOH/DCM gradient as eluant. To a solution of the free amine in EtOAc was added one equivalent of HCl in dioxan (0.125 mL, 4M) causing the hydrochloride salt to precipitate out. The salt was filtered and washed thoroughly with ether before repeated triturations with EtOAc/ether mixtures yielded 8 (ii) as a crystalline white solid (0.117 g, 41%).

$^1$H NMR (DMSO): δ 1.27 (3H, s, αC$\underline{H}_3$), 2.68 (6H, bs, N(C$\underline{H}_3$)$_2$), 3.12 (1H, d, 14.6 Hz, CH$\underline{H}$ indole), 3.31–3.36 (1H, m, (obscured by water peak) CH$\underline{H}$NHCO), 3.37 (1H, d, 14.2 Hz, CH$\underline{H}$ indole), 3.49–3.56 (1H, m, CH$\underline{H}$NHCO), 3.72 (1H, d, 15.6 Hz, OCOC$\underline{H}$HN (CH$_3$)$_2$), 3.81 (1H, d, 15.6 Hz, OCOC$\underline{H}$HN(CH$_3$)$_2$), 5.03 (1H, q, 8.1, 14.4 Hz, NHC$\underline{H}$CHHNH), 5.13 (1H, d, 13.4 Hz, C$\underline{H}$HOCONH), 5.19 (1H, d, 13.4 Hz, CH$\underline{H}$OCONH), 6.79 (1H, t, 7.3 Hz, Ar$\underline{H}$), 6.87 (1H, s, OCON$\underline{H}$), 6.95 (2H, t, 7.1 Hz, Ar$\underline{H}$), 7.17–7.31 (9H, m, Ar$\underline{H}$), 7.40 (1H, d, 7.8 Hz, Ar$\underline{H}$), 7.52 (1H, d, 7.8 Hz, Ar $\underline{H}$), 7.61 (1H, d, 7.6 Hz, Ar$\underline{H}$), 8.16 (1H, d, 8.5 Hz, CON$\underline{H}$CH), 8.48 (1H, m, CHHN$\underline{H}$CO), 9.68 (1H, s, $\underline{H}^+$Cl–), 10.82 (1H, s, indole N$\underline{H}$);

IR: 3334.0, 1715.7, 1682.0, 1652.0, 1540.3, 1455.0, 1252.0 cm$^{-1}$;

$α^D$=–46.45, (MEOH, c=0.155 g, 100 mL$^{-1}$); mp 126°–128° C.;

Anal. C$_{34}$H$_{38}$ClN$_5$O$_5$·1.0H$_2$O: C,H,N.

EXAMPLE 11

Compound 10 (i)

To a stirred solution of boc-(L)-leu(OH) (0.32 g, 1.37 mmol) and 2-(1H-benzotriazol-1-yl) 1, 1,3, 3-tetramethyluronium hexafluorophosphate (HBTU) (0.52 g, 1.37 mmol) in DMF (10 mL) at room temperature was added diisopropylethylamine (238 µL, 1.37 mmol). After 10 minutes, 7 (vi) (799 mg, 1.37 mmol), diisopropylethylamine (238 µL, 1.37 mmol), and dimethylaminopyridine (167 mg, 1.37 mmol) were added to the reaction mixture which was stirred for a further 10 hours. The solvent was removed under reduced pressure and the residue was taken up in EtOAc and washed with 10% citric acid solution, water, NaHCO$_3$(aq), water, brine, dried (MgSO$_4$), and concentrated in vacuo. The residue was chromatographed on silica gel eluting with CH$_2$Cl$_2$ to give 10 (i) (695 mg, 70%).

$^1$H NMR (CDCl$_3$): δ 0.83–0.90 (6H, m, CH(C$\underline{H}_3$)$_2$), 1.42 (9H, s, $^t$butyl), 1.63 (3H, s, αC$\underline{H}_3$), 1.40–1.65 (3H, m, C$\underline{H}$C$\underline{H}_2$(CH$_3$)$_2$), 3.30 (1H, d, 14.6 Hz, CH$\underline{H}$ indole), 3.53 (1H, d, 14.6 Hz, CH$\underline{H}$ indole), 4.20–4.30 (3H, m, C$\underline{H}$HO, COC $\underline{H}$N), 4.94 (1H, bd, 7.8 Hz, OCON$\underline{H}$CH), 5.16 (1H, d, 13.2 Hz, CH$\underline{H}$OCONH), 5.24 (1H, d, 13.4 Hz, CH$\underline{H}$OCONH), 5.20–5.25 (1H, m, PhC$\underline{H}$NH), 5.58 (1H, s, OCON$\underline{H}$C), 6.77 (1H, s, Ar$\underline{H}$), 6.83 (2H, s, Ar$\underline{H}$, CON$\underline{H}$CHPh), 7.03–7.08 (1H, m, Ar$\underline{H}$), 7.13–7.33 (9H, m, Ar$\underline{H}$), 7.47 (1H, d, 8.1 Hz, Ar$\underline{H}$), 7.55–7.60 (2H, m, Ar$\underline{H}$), 8.23 (1H, s, indole N$\underline{H}$);

IR: 3346.0, 2959.0, 1714.0, 1665.0, 1505.0, 1455.0, 1368.0, 1250.0, 1162.0, 1070.0, 742.0 cm$^{-1}$;

$α^D$=+10.9 (MEOH, c=0.5 g, 100 mL$^{-1}$); mp 73°–78° C.;

Anal. C$_{41}$H$_{48}$N$_4$O$_8$: C,H,N.

EXAMPLE 12

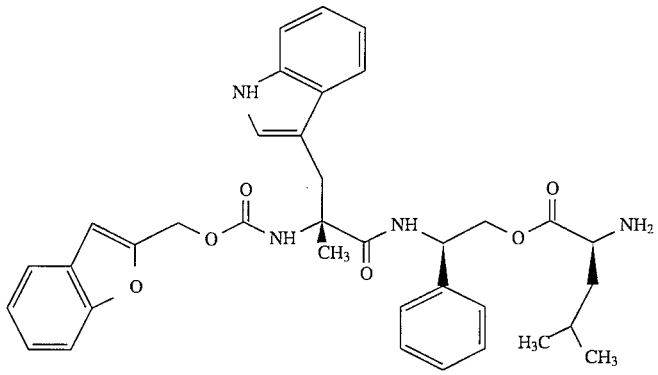

L-Leucine,
2-[[2-[[(2-benzofuranylmethoxy)carbonyl]amino]-
3-(1H-indol-3-yl)-2-methyl-1-oxopropyl]amino]-
2-phenylethyl ester, [R-(R*,R*)]-

Compound 11 (i)

To a solution of formic acid (20 mL), anisole (1 mL), and water (1 mL) was added 10 (i) (0.63 g, 0.87 mmol) and the mixture was stirred for 2 hours. The solvent was removed and the residue was taken up in EtOAc and washed with NaHCO$_{3(aq)}$, brine, dried (MgSO$_4$), and concentrated in vacuo. The residue was purified by flash chromatography on silica gel eluting with EtOAc to yield the free amine (608 mg, 80%). To a solution of the free amine (538 mg, 0.86 mmol) in ether (80 mL) was added a solution of HCl in dioxan (0.25 mL, 1 mmol) causing the hydrochloride salt, 11 (i), to precipitate out immediately as a white solid. The mixture was stirred for 20 minutes before the solid was removed by filtration to give 11 (i) (520 mg, 91%).

$^1$H NMR (CDCl$_3$): δ 0.70–0.80 (6H, m, CH(C$\underline{H}_3$)$_2$), 1.50–1.80 (6H, m, C$\underline{H}$C$\underline{H}_2$(CH$_3$)$_2$, αC$\underline{H}_3$), 3.31 (1H, d, 14.9 Hz, CH$\underline{H}$ indole), 3.48 (1H, d, 14.4 Hz, CH$\underline{H}$ indole), 3.80–3.90 (1H, m, C$\underline{H}$NH$_3^+$), 3.98–4.18 (1H, m, CHCH $\underline{H}$O), 4.37–4.43 (1H, m, CHC$\underline{H}$HO), 5.10–5.25 (3H, m, C $\underline{H}$HOCONH, PhC$\underline{H}$NH), 5.80–6.00 (1H, bs, OCON$\underline{H}$), 6.72 (1H, s, Ar$\underline{H}$), 6.80–7.00 (1H, bs, CON$\underline{H}$CHPh), 6.95–7.30 (11H, m, Ar$\underline{H}$), 7.42 (1H, d, 8.3 Hz, Ar$\underline{H}$), 7.48–7.54 (2H, m, Ar$\underline{H}$), 8.55 (1H, s, indole N$\underline{H}$);

IR: 3350.0–3100.0, 2961.0, 1732.0, 1661.0, 1505.0, 1455.0, 1250.0, 1135.0, 1070.0, 742.0 cm$^{-1}$;

MS m/e (CI) 625 (M+H), 624 (M);

$α^D$=+2.30° (MEOH, c=0.5 g, 100 mL$^{-1}$); mp 110°–115° C.;

HPLC R.T.=10.85, C$^{18}$ reverse phase, 40–100% MeCN:TFA/H$_2$O:TFA;

Anal. C$_{36}$H$_{40}$N$_4$O$_6$·HCl: C,H,N.

EXAMPLE 13

Compound 13

The carbonate salt of the amine (12) (Horwell, et al., *J. Med. Chem.* 34: 404 (1991)) (1.0 g, 3.3 mmol) was suspended in dioxan (20 mL) containing water (2 mL) and cooled to 0° C. Potassium Hydroxide pellets (0.5 g, 8.9 mmol) and ditertbutylcarbonate (1.3 g, 6.0 mmol) were then added to the reaction mixture which was stirred at 0° C. for 1 hour and at room temperature for a further hour. The reaction mixture was poured onto water (150 mL), extracted with EtOAc (2×75 mL), dried (MgSO$_4$), and evaporated in vacuo to yield an oily residue. The residue was purified by flash chromatography using EtOAc/hexane 0–100% gradient as eluant to give the desired Product 13 as a white solid (1.12 g, 82%).

$^1$H NMR (DMSO): δ 1.33 (9H, s, Boc), 3.17 (2H, t, 6.24 Hz, CH$_2$NH$_2$), 4.69 (1H, q, 7.4, 15.5 Hz, CHCHH), 4.96 (1H, d, 12.6 Hz, PhCHHOCON), 5.02 (1H, d, 12.6 Hz, PhCHHOCON), 6.84 (1H, m, NHBoc), 7.08–7.33 (10H, m, ArH), 7.72 (1H, d, 8.4 Hz, NHCOOCHH);

IR: 271.0, 240.0, 91.0 cm$^{-1}$;

MS m/e (CI)371 (M+H);

Anal. C$_{21}$H$_{26}$N$_2$O$_4$: C,H,N.

EXAMPLE 14

Compound 14

The protected diamine (13) (0.5 g, 1.4 mmol) was dissolved in MeOH (50 mL) and hydrogenated at 45 psi/30° C. in a parr apparatus using 10% palladium on carbon (50 mg) as the catalyst. The reaction was complete after 2 hours and the catalyst was removed by filtration through celite and the solvent removed in vacuo to yield 14 as a viscous brown oil (0.32 g, 100%).

$^1$H NMR (DMSO): δ 1.36 (9H, s, Boc), 2.89–2.98 (1H, m, CHHNHBoc), 3.07–3.17 (1H, m, CHHNHBoc), 3.85–3.89 (1H, m CHCHH), 6.44–6.78 (1H, m NHBoc), 7.17–7.35 (6H, m, ArH, NHH);

IR: 164.0, 106.0;

MS m/e (CI) 237 (M+H), 181 (100%).

EXAMPLE 15

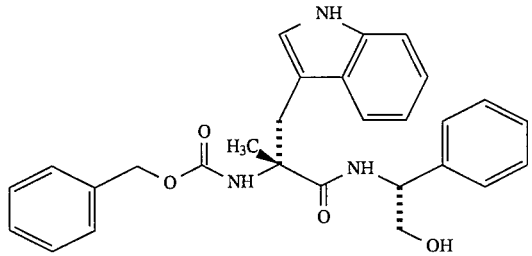

Carbamic acid, [2-[(2-hydroxy-1-phenylethyl)amino]-1-(1H-indol-3-ylmethyl)-1-methyl-2-oxoethyl]-, phenylmethyl ester, [R-(R* R*)]-

Compound 7 (i)

$^1$H NMR (CDCl$_3$): δ 1.67 (3H, s, αCH$_3$), 2.60 (1H, bs, OH), 3.23 (1H, d, 14.7 Hz, CHH indole), 3.42 (1H, d, 14.7 Hz, CHH indole), 3.61–3.74 (2H, m, CHHOH), 5.00 (1H, m, CHCH$_2$OH), 5.04 (1H, d, 12.4 Hz, CHHOCONH), 5.11 (1H, d, 12.2 Hz, CHHOCONH), 5.41 (1H, s, NHCO$_2$CH$_2$), 6.54 (1H, d, 7.6 Hz, CONHCH), 6.89 (1H, s, ArH), 7.10–7.36 (13H, m, ArH), 7.59 (1H, d, 7.9 Hz, ArH), 8.05 (1H, s, indole NH);

IR: 3807.0, 1704.0, 1632.0, 1504.0, 1455.0, 1253.0, 1105.0, 1073, 740.0, 697.0 cm$^{-1}$;

Anal. C$_{28}$H$_{29}$N$_3$O$_4$: C,H,N.

EXAMPLE 16

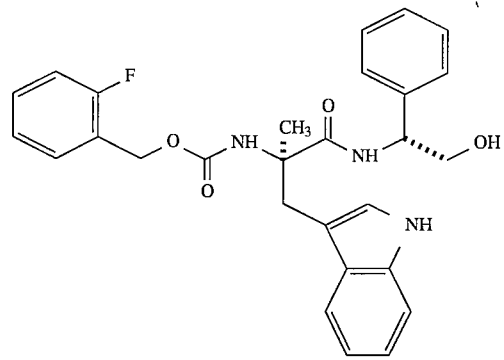

Carbamic acid, [2-[(2-hydroxy-1-phenylethyl)amino]-1-(1H-indol-3-ylmethyl)-1-methyl-2-oxoethyl]-, (2-fluorophenyl)methyl ester, [R-(R*,R*)]-

Compound 7 (ii)

$^1$H NMR (CDCl$_3$): δ 1.66 (3H, s, αCH$_3$), 2.65 (1H, bs, OH), 3.25 (1H, d, 14.4 Hz, CHH indole), 3.42 (1H, d, 14.8 Hz, CHH indole), 3.62–3.68 (1H, m CHHOH), 3.70–3.80 (1H, m, CHHOH), 5.00 (1H, m, CHCH$_2$OH), 5.12 (1H, d, 12.4 Hz, CHHOCONH), 5.20 (1H, d, 12.4 Hz, CHHOCONH), 5.45 (1H, s, NHCO$_2$CH$_2$), 6.56 (1H, d, 8.0 Hz, CONHCH), 6.92 (1H, d, 2.4 Hz, ArH), 7.05–7.39 (12H, m, ArH), 7.59 (1H, d, 8.0 Hz, ArH), 8.12 (1H, s, indole NH);

IR: 3340.0, 1709.0, 1660.0, 1495.0, 1456.0, 1234.0, 1073.0 cm$^{-1}$;

MS m/e (FAB) 490.4 (M+H), 512.3 (M+Na);

α$^D$=+25.53 (MEOH, c=0.38 g, 100 mL$^{-1}$); mp 146.5°–147.5° C.;

HPLC R.T.=11.208, C$^{18}$ reverse phase, 40–100% MeCN: TFA/water:TFA;

Anal. C$_{28}$H$_{28}$FN$_3$O$_4$.0.6H$_2$O: C,H,N.

EXAMPLE 17

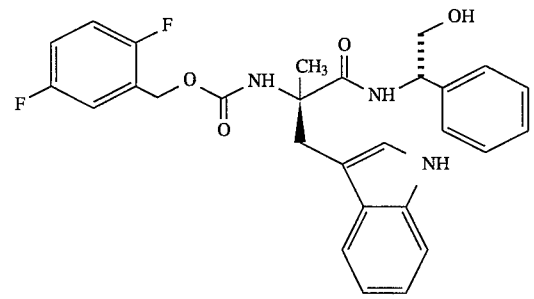

Carbamic acid, [2-[(2-hydroxy-1-phenylethyl)amino]-1-(1H-indol-3-ylmethyl)-1-methyl-2-oxoethyl]-, (2,5-difluorophenyl)methyl ester, [R-(R*,R*)]

Compound 7 (iii)

$^1$H NMR (CDCl$_3$): δ 1.70 (3H, s, αCH$_3$), 2.42 (1H, bs, OH), 3.28 (1H, d, 14.4 Hz, CHH indole), 3.46 (1H, d, 14.8 Hz, CHH indole), 3.66–3.80 (2H, m, CHHOH), 5.00 (1H, m, C HCH₂OH), 5.10 (1H, d, 13.0 Hz, CHHOCONH), 5.16 (1H, d, 12.8 Hz, CHHOCONH), 5.53 (1H, s, NHCO₂CH₂), 6.53 (1H, d, 7.5 Hz, CONHCH), 6.97–7.36 (11H, m, ArH), 7.37 (1H, d, 8.1 Hz, ArH), 7.61 (1H, d, 7.9 Hz, ArH), 8.00 (1H, s, indole NH);

IR: 3332.0, 1714.0, 1660.7, 1496.0, 1248.0, 1072 cm⁻¹;

MS m/e (FAB) 508.5 (M+H);

$\alpha^D$=+20.00 (MEOH, c=0.045 g, 100 mL⁻¹); mp 136°–139° C.;

Anal. $C_{28}H_{27}F_2N_3O_4$: C,H,N.

(1H, d, 7.8 Hz, ArH), 7.74 (1H, dd, 6.35, 5.37 Hz, ArH), 7.79 (1H, dd, 6.35 Hz, ArH), 7.96 (1H, s, indole NH);

IR: 3375.0, 1705.0, 1653.0, 1495.0, 1457.0 cm⁻¹;

MS m/e (FAB) 528.0 (M+H), 550.6 (M+Na);

$\alpha^D$=+31.43 (MEOH, c=0.07 g, 100 mL⁻¹); mp 77°–82° C.;

Anal. $C_{30}H_{29}N_3O_4S$: C,H,N.

EXAMPLE 19

[2-(1H)-Indol-3-yl)-1-methyl-1-(1-phenyl-2-phosphonooxy-ethylcarbamoyl)-ethyl]-carbamic acid benzofuran-2-ylmethyl ester monosodium salt

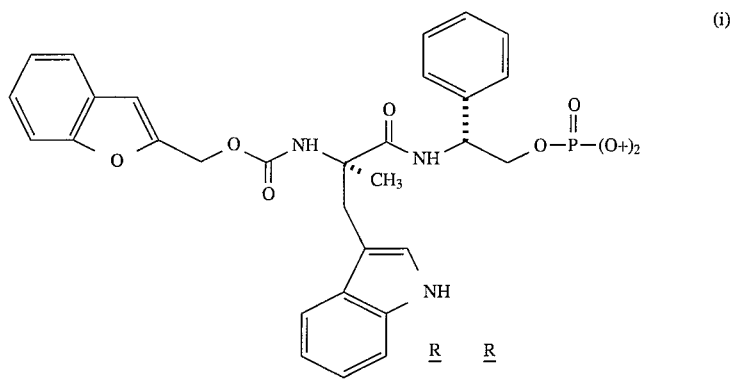

(i)

EXAMPLE 18

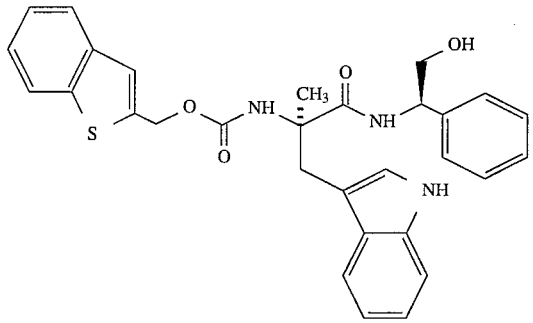

Carbamic acid, [2-[(2-hydroxy-1-phenylethyl)amino]-1-(1H-indol-3-ylmethyl)-1-methyl-2-oxoethyl]-, benzo[b]thien-2-ylmethyl ester, [R-(R*,R*)]-

Compound 7 (v)

¹H NMR (CDCl₃): δ 1.69 (3H, s, αCH₃), 2.53 (1H, bs, OH), 3.24 (1H, d, 14.8 Hz, CHH indole), 3.43 (1H, d, 14.8 Hz, CHH indole), 3.60–3.68 (1H, m, CHHOH), 3.70–3.79 (1H, m, CHHOH), 5.00 (1H, m, CHCH₂OH), 5.26 (1H, d, 12.8 Hz, CHHOCONH), 5.37 (1H, d, 12.8 Hz, CHHOCONH), 5.46 (1H, s, NHCO₂CH₂), 6.49 (1H, d, 7.6 Hz, CONHCH), 6.91 (1H, s, ArH), 7.09–7.36 (11H, m, ArH), 7.59

To a stirred solution of the compound from Example 18 (5.12 g, 10 mmol) and di-t-butyl-N,N-diethyl phosphoramidite (4.02 g, 15 mmol) in dry THF (30 mL), cooled in an ice bath, was added 1-H-tetrazole (2.10 g, 30 mmol) in one portion. After stirring for 5 minutes, the ice bath was removed and the reaction mixture stirred at room temperature for a further 90 minutes. The solution was then cooled to −50° C., and a solution of m-chloroperoxybenzoic acid (~95%, 2.72 g, 15 mmol) in dry THF (10 mL) was added dropwise rapidly, ensuring that the reaction temperature was kept below 0° C. The mixture was stirred at room temperature for 20 minutes and then 10% aqueous NaHSO₃ (50 mL) was added, the mixture stirred for a further 15 minutes before transferring to a separating funnel and washing with 10% aqueous NaHSO₃ (2×50 mL), brine (1×50 mL), drying over MgSO₄, filtering, and removing the solvent in vacuo. The crude residue was then purified by chromatography (silica gel, MeOH-CH₂Cl₂ (0.5% pyridine gradient 0–2.5%) giving the product as a colorless oil (containing some residual pyridine (3.51 g, 50%).

IR (film): 3295, 1728, 1668, 1455, 1250, 1040, 1006, 742 cm⁻¹.

NMR ¹H (CDCl₃): δ 1.36 (9H, s), 1.49 (9H, s), 1.68 (3H, s), 3.43 (1H, d, J=14.6 Hz, 3.56 (1H, d, J=14.6 Hz), 4.11 (2H, m), 5.08 (1H, m), 5.20 (2H, s), 5.76 (1H, s), 6.75 (1H, m), 6.88 (1H, m), 7.02–7.70 (13H, m), 8.21 (1H, s).*

*NMR ³¹P (CDCl₃, 162 Hz)—8.6 ppm (1P, t, J=8 Hz).

FAB-MS M+H: 704 (weak), M+Na: 726.

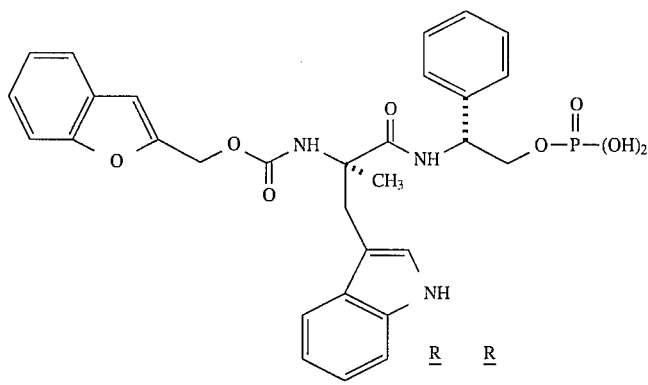

The phosphate ester (3.50 g, 4.98 mmol) was treated with formic acid (20 mL) for 3 hours at room temperature and then the solvent removed in vacuo. The resulting crude acid was then purified by chromatography (reverse phase silica gel, MeCN-H$_2$O, gradient 0–40%) to give the pure product (1.64 g, 56%) as an off-white foam, mp 98°–105° C.

IR (film): 3383, 1715, 1652, 1495, 1455, 1251, 1071, 743 cm$^{-1}$.

NMR $^1$H (CDCl$_3$): δ 1.50 (3H, s), 3.28 (2H, m), 4.05 (2H, br.s), 5.05 (3H, m), 5.89 (1H, s), 6.53–7.53 (16H, m), 8.78 (1H, br.s).

NMR $^{31}$P (CDCl$_3$, 162 MHz): δ 0.79 (br.s) HPLC (Ultrasphere C18, 5μ, 4.6×250 mm), MeCN-H$_2$O (0.1% TFA), gradient 40–100% (20 minutes, 1 mL/min$^{-1}$), RT=9.7 minutes (>99%). CI-MS.

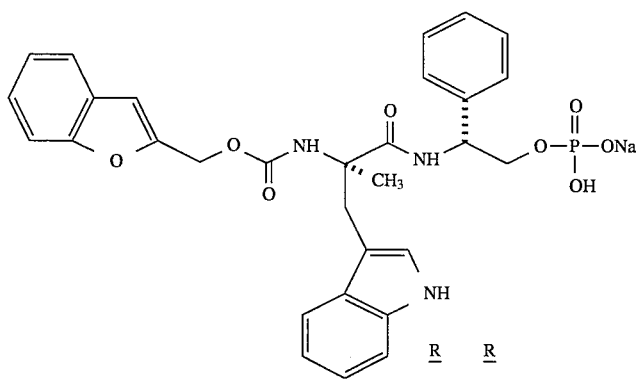

To a stirred solution of the phosphate acid (296 mg, 0.5 mmol) in acetone (150 mL) was added 0.05N aqueous NaOH (10.0 mL, 0.5 mmol) dropwise over a period of 10 minutes (the flask containing the aqueous NaOH being washed into the reaction flask with 3×1 mL portions H$_2$O). The mixture was stirred at room temperature for 20 minutes and the acetone removed in vacuo; the resulting 'hazy' solution was diluted with H$_2$O (H$_2$O) and then lyophilized to give the phosphate-monosodium salt (272 mg, 89%) as an off-white solid, mp 147°–151° C.

IR (film): 3391, 3060, 2938, 1705, 1652, 1495, 1455, 1251, 1071, 743 cm$^{-1}$.

NMR (D$_2$O): δ 1.38 (3H, br.s), 3.16 (1H, m), 3.24 (1H, m), 4.00 (2H, m), 5.06 (3H, m), 6.68 (1H, br.s), 6.84–7.48 (17H, m).

NMR $^{31}$P (D$_2$O, 162 MHz): +1.6 (IP, br.s.).

Analysis (C$_{30}$H$_{29}$N$_3$O$_8$PNa.1H$_2$O): C, H, N, P, Na.

HPLC (Ultrasphere C18, 5μ, 4.6×250 mm). MeCN-H$_2$O (0.1% TFA), gradient 40–100% (20 minutes, 1 mL/min$^{-1}$), RT 9.73 (>98%). FAB-MS M+H: 614. M+Na: 636.

We claim:

1. A compound of formula

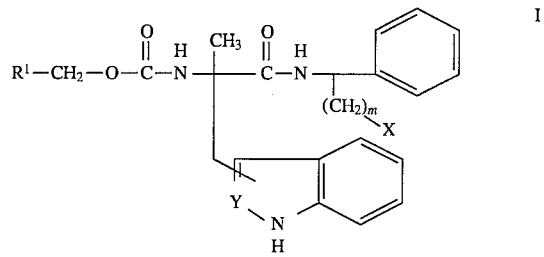

or a pharmaceutically acceptable salt thereof wherein

R$^1$ is phenyl, pyridyl, thienyl, furanyl, naphthyl, indolyl, benzofuranyl, or benzothienyl each unsubstituted, mono-, di-, or trisubstituted by alkyl, hydroxy, alkoxy, nitro, halogen, amino, or trifluoromethyl;

X is OR$^2$ wherein R$^2$ is hydrogen, (CH$_2$)$_n$NR$_3$R$_4$, or a promoiety, or X is NH$_2$,
NHCO-promoiety,
NHCO(CH$_2$)$_n$NR$_3$R$^4$,
NR$^3$R$^4$, or
(CH$_2$)$_n$NR$^3$R$^4$ wherein n is an integer of from 0 to 5 and R$^3$ and R$^4$ are each independently selected from hydrogen and methyl;

m is an integer of from 1 to 6; and

Y is CH, CCH$_3$, CF, CCl, CBr, CSCH$_3$, or N.

2. A compound according to claim 1 wherein

R$^1$ is phenyl, pyridyl, thienyl, furanyl, naphthyl, indolyl, benzofuranyl, or benzothienyl each unsubstituted or mono-, di-, or trisubstituted by alkyl, hydroxy, alkoxy, nitro, halogen, amino, or trifluoromethyl;

X is OR² wherein R² is hydrogen, —COCH₂N(CH₃)₂, —COC(CH₃)₂N(CH₃)₂, —COCH[CH₂CH(CH₃)₂]NH₂, —COCH₂CH₂CO₂H,

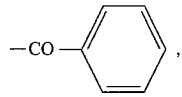

—COC(CH₃)₃, —COMe, —COOC(CH₃)₃, —COCH(CH₂CO₂H)NH₂, —PO₃H₂,

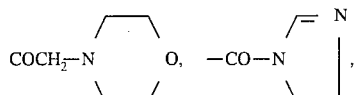

—CO—C(CH₃)—NH—COOC(CH₃)₃,

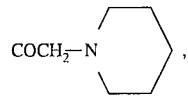

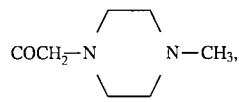

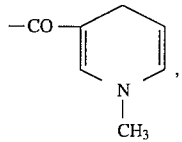

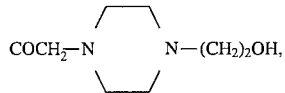

—(CH₂)ₙNR³R⁴, —CHR⁵NR³R⁴ wherein R⁵ is a side chain of a genetically coded amino acid;

X is NHCO(CH₂)ₙNR³R⁴ or NR³R⁴ wherein n is an integer of from 0 to 5 and R³ and R⁴ are each independently hydrogen or methyl;

m is 1; and

Y is CH, CCH₃, CF, CCl, CBr, CSCH₃, or N.

3. A compound of formula

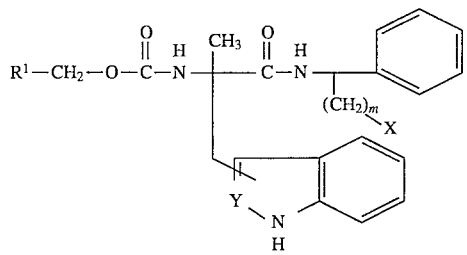

wherein

R¹ is phenyl, 2-benzofuranyl, 2-fluorophenyl, 2,5-difluorophenyl, 2-benzothienyl, or 4-CH₃; 2-fluorophenyl;

X is OR² wherein R² is hydrogen, or a promoiety selected from: COCH(CH₂(CH₃)₂)NH₂, or COCH₂N(CH₃)₂,

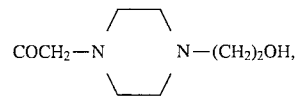

PO₃H₂, or or X is NH₂ or NHCH₃;

m is 1; and

Y is CH.

4. A compound selected from

Carbamic acid, [2-[(2-hydroxy-1-phenylethyl)amino]-1-(1H-indol-3-ylmethyl)-1-methyl-2-oxoethyl]-, 2-benzofuranylmethyl ester, [R-(R*,R*)]-;

Carbamic acid, [2-[(2-hydroxy-1-phenylethyl)amino]-1-(1H-indol-3-ylmethyl)-1-methyl-2-oxoethyl]-, (2-fluorophenyl)methyl ester, [R-(R*,R*)]-;

Carbamic acid, [2-[(2-hydroxy-1-phenylethyl)amino]-1-(1H-indol-3-ylmethyl)-1-methyl-2-oxoethyl]-, benzo[b]thien-2-ylmethyl ester, [R-(R*,R*)]-;

L-Leucine, 2-[[2-[[(2-benzofuranylmethoxy)carbonyl]amino]-3-(1H-indol-3-yl)-2-methyl-1-oxopropyl]amino]-2-phenylethyl ester, [R-(R*,R*)]-;

Carbamic acid, [2-[(2-amino-1-phenylethyl)amino]-1-(1H-indol-3-ylmethyl)-1-methyl-2-oxoethyl]-, 2-benzofuranylmethyl ester, [R-(R*,R*)]-;

Carbamic acid, [2-[(2-amino-1-phenylethyl)amino]-1-(1H-indol-3-ylmethyl)-1-methyl-2-oxoethyl]-, 2-benzofuranylmethyl ester, [R-(R*,R*)]-;

Carbamic acid, [1-(1H-indol-3-ylmethyl)-1-methyl-2-oxo-2-[(1-phenylethyl)amino]ethyl]-, phenylmethyl ester, [R-(R*,R*)]-;

Carbamic acid, [2-(2-hydroxy-1-phenylethyl)amino]-1-(1H-indol-3-ylmethyl)-1-methyl-2-oxoethyl]-, 2-benzofuranylmethyl ester, [R-(R*,R*)]-;

Carbamic acid, [2-[[(2-[[(dimethylamino)acetyl]amino]-1-phenylethyl]amino]-1-(1H-indol-3-ylmethyl)-1-methyl-2-oxoethyl]-, 2-benzofuranylmethyl ester, monohydrochloride, [R-(R*,R*)]-.

5. A compound selected from:

Carbamic acid, [2-[(2-hydroxy-1-phenylethyl)amino]-1-(1H-indol-3-ylmethyl)-1-methyl-2-oxoethyl]-, (2,5-difluorophenyl)methyl ester, [R-(R*,R*)]; and Glycine, N,N-dimethyl-, 2-[[2-[[(2-benzofuranylmethoxy)carbonyl]amino]-3-(1H-indol-3-yl)-2-methyl-1-oxopropyl]amino]-2-phenylethyl ester, monohydrochloride, [R-(R*,R*)]-.

6. A compound named [2-(1H)-indol-3-yl)-1-methyl-1-(1-phenyl-2-phosphonooxy-ethylcarbamoyl)-ethyl]carbamic acid benzofuran-2-ylmethyl ester monosodium salt.

7. A compound of formula

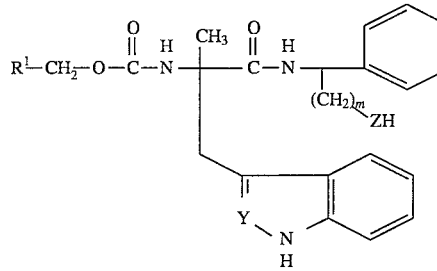

wherein

R¹ is phenyl, pyridyl, thiophenyl, furanyl, naphthyl, indolyl, benzofuranyl, or benzothienyl each unsubstituted or mono-, di-, or trisubstituted by alkyl, hydroxy, alkoxy, nitro, halogen, amino, or trifluoromethyl;

m is an integer of from 1 to 6; and,

Y is CH, CCH$_3$, CF, CCl, CB$_r$, CSCH$_3$, or N; and

Z is oxygen or NH.

8. A pharmaceutical composition comprising an amount of a compound according to claim 1 effective to treat disorders in a mammal suffering therefrom, and a pharmaceutically acceptable carrier.

9. A method for treating respiratory disorders in a mammal comprising administering a therapeutically effective amount of a compound according to claim 1.

10. A method for treating asthma in a mammal comprising administering a therapeutically effective amount of a compound according to claim 1.

11. A method for treating inflammation in a mammal comprising administering a therapeutically effective amount of a compound according to claim 1.

12. A method for treating arthritis in a mammal comprising administering a therapeutically effective amount of a compound according to claim 1.

13. A method for treating gastrointestinal disorders in a mammal comprising administering a therapeutically effective amount of a compound according to claim 1.

14. A method for treating ophthalmic diseases in a mammal comprising administering a therapeutically effective amount of a compound according to claim 1.

15. A method for treating allergies in a mammal comprising administering a therapeutically effective amount of a compound according to claim 1.

16. A method for treating diseases of the central nervous system in a mammal comprising administering a therapeutically effective amount of a compound according to claim 1.

17. A method for treating migraine in a mammal comprising administering a therapeutically effective amount of a compound according to claim 1.

18. A method for treating inflammatory pain or neurogenic inflammation in a mammal comprising administration of therapeutically effective amounts of a compound according to claim 1.

19. A method for treating rheumatoid arthritis in a mammal comprising administration of therapeutically effective amounts of a compound according to claim 1.

20. A method for treating atherosclerosis in a mammal comprising administration of therapeutically effective amounts of a compound according to claim 1.

21. A method for treating tumor cell growth in a mammal comprising administration of therapeutically effective amounts of a compound according to claim 1.

22. A method for treating and/or preventing emesis in a mammal comprising administration of a therapeutically effective amount of a compound according to claim 1.

23. A method for treating multiple sclerosis in a mammal comprising administration of a therapeutically effective amount of a compound according to claim 1.

24. A method of using a compound according to claim 1 as a diagnostic in imaging NK$_1$ receptors in vivo.

25. A method of antagonizing NK$_1$ receptors by administering a compound according to claim 1.

* * * * *